United States Patent [19]
Van Der Brug et al.

[11] Patent Number: 6,006,127
[45] Date of Patent: Dec. 21, 1999

[54] IMAGE-GUIDED SURGERY SYSTEM

[75] Inventors: Willem P. Van Der Brug; Hubrecht L.T. De Bliek; Frans A. Gerritsen, all of Eindhoven, Netherlands

[73] Assignee: U.S. Philips Corporation, New York, N.Y.

[21] Appl. No.: 09/030,484

[22] Filed: Feb. 25, 1998

[30] Foreign Application Priority Data

Feb. 28, 1997 [EP] European Pat. Off. .............. 97200600

[51] Int. Cl.⁶ ....................................................... A61B 5/00
[52] U.S. Cl. ........................ 600/427; 600/426; 600/429; 606/130
[58] Field of Search ................................... 600/407, 426, 600/427, 429, 414, 411, 417; 606/130

[56] References Cited

U.S. PATENT DOCUMENTS

| | | | |
|---|---|---|---|
| 5,299,288 | 3/1994 | Glassman et al. | 395/80 |
| 5,494,034 | 2/1996 | Schlondorff et al. | 128/653.1 |
| 5,638,819 | 6/1997 | Manwaring et al. | 128/653.1 |
| 5,662,111 | 9/1997 | Cosman | 128/653.1 |
| 5,676,673 | 10/1997 | Ferre et al. | 606/130 |
| 5,755,725 | 5/1998 | Druais | 606/130 |
| 5,762,458 | 6/1998 | Wang et al. | 414/1 |
| 5,776,064 | 7/1998 | Kalfas et al. | 600/414 |
| 5,817,105 | 10/1998 | Van Der Burg | 606/130 |
| 5,836,954 | 11/1998 | Heilbrun et al. | 606/130 |
| 5,851,183 | 12/1998 | Bucholz | 600/425 |

FOREIGN PATENT DOCUMENTS

| | | | |
|---|---|---|---|
| 0676178A1 | 10/1995 | European Pat. Off. | A61B 19/00 |
| 0755660A2 | 1/1997 | European Pat. Off. | A61B 19/00 |

*Primary Examiner*—Ruth S. Smith
*Attorney, Agent, or Firm*—Dwight H. Renfrew, Jr.

[57] ABSTRACT

An image-guided surgery system is used to show a user, for example a surgeon, a position of a surgical instrument in an operating area in the body of a patient during a surgical operation. The image-guided surgery system includes an alignment system for deriving an alignment line through a target position, for selecting a starting plane through an end of the surgical instrument, for deriving a starting point on the alignment line and in the starting plane, and for reproducing a position of said end and of said starting point relative to one another in the starting plane. For example, the positions of the end and the starting point in the starting plane are reproduced in a guide image.

14 Claims, 1 Drawing Sheet

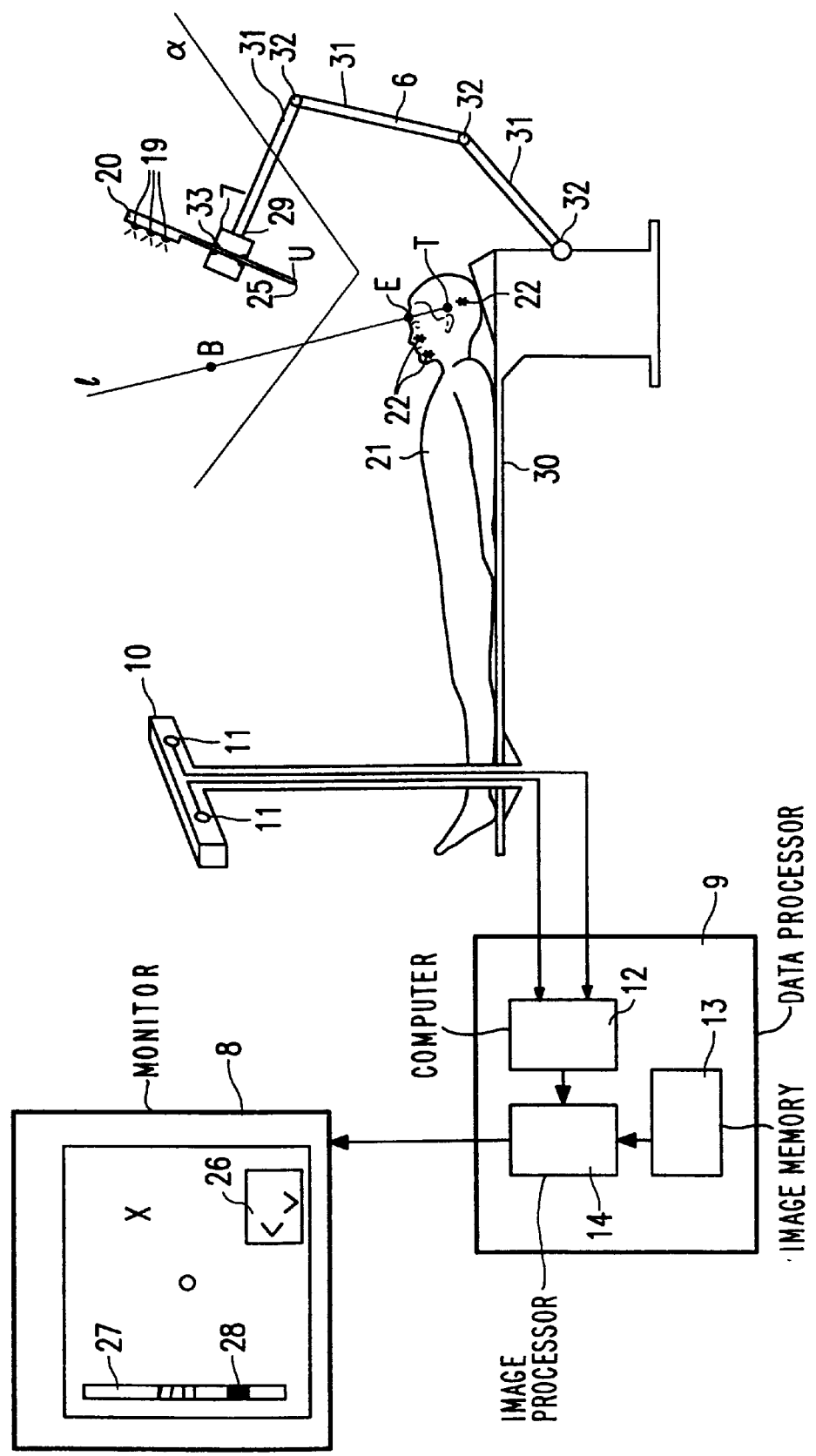

IMAGE-GUIDED SURGERY SYSTEM

BACKGROUND OF THE INVENTION

1. Field of the Invention

The invention relates to an image-guided surgery system.

2. Description of Related Art

An image-guided surgery system of this kind is known from United States patent specification U.S. Pat. No. 5,389, 101.

An image-guided surgery system is used to visualize a position of a surgical instrument in an operating area within the body of a patient for a surgeon during surgery. Images, such as CT or MRI images, are made of the patient prior to surgery. The image-guided surgery system includes a position-measuring system for measuring the position of the surgical instrument. The image-guided surgery system also includes a computer for deriving corresponding positions in a relevant image from the positions of the surgical instrument measured. During surgery the position measuring system measures the position of the surgical instrument relative to the patient and the computer calculates the position in such a prior image which corresponds to the measured position of the surgical instrument. The prior image is then displayed on a monitor, together with the actual position of the surgical instrument. The surgeon can see the position of the surgical instrument in the operating area in the image on the monitor, without him or her seeing the surgical instrument directly. The surgeon can thus observe the image displayed on the monitor so as to see how to move the surgical instrument in the operating area without substantial risk of unnecessary damaging of tissue, and notably without risk of damaging of vital parts.

An image-guided surgery system of this kind is used, for example in neurosurgery in order to show the surgeon accurately where the surgical instrument is situated in the brain during a cerebral operation.

Using the known image-guided surgery system it is difficult to position the instrument with one end in a desired position. In order to move the instrument to the desired position, it is necessary to move it whereas at the same time the image showing the position of the surgical instrument relative to the patient must be observed so as to determine whether the desired position has been reached. It has been found that accurate positioning of the instrument requires a substantial amount of training and that these operations remain time consuming still.

SUMMARY OF THE INVENTION

It is an object of the invention to provide an image-guided surgery system in which accurate positioning of the surgical instrument is easier and faster.

This object is achieved by means of an image-guided surgery system according to the invention which includes an alignment system for deriving an alignment line through a target position, for selecting a starting plane through an end of a surgical instrument, for deriving a starting point on the alignment line and in the starting plane, and for reproducing a position of said end and of said starting point relative to one another in the starting plane.

The target position is a position which is usually situated in or on the body of the patient and whereto the end of the surgical instrument is to be guided during a given phase of the operation. During the operation, the surgical instrument is introduced into the body of the patient via an entrance position on the surface. The target position may in some cases be the final position to be ultimately reached by the end of the surgical instrument. At the final position there is situated, for example a tumor to be removed. More generally speaking, however, the target position is situated somewhere between the final position and the entrance position, for example, when the final position is to be reached along a curved path extending from the entrance position. The alignment line passes through the target position and has a direction via which the target position can be readily approached. For example, the alignment line extends through the entrance position and the target position. The user preferably chooses the entrance position so that the target position can be readily reached from the entrance position. At the beginning of the surgical intervention the surgical instrument is positioned at the starting point. This can be very readily achieved by moving the end of a surgical instrument in the starting plane until this end reaches the starting point. The alignment system shows the user how to move the end to the starting point. To this end, the alignment system shows, for example the positions of the end and the starting point in the starting plane. The positions of the starting point and the end of the surgical instrument can be revealed to the user in various ways. For example, it is very simple to state the co-ordinates of the starting point and the end of the surgical instrument in the starting plane. It is particularly attractive to display a guide image on an image display unit such as a monitor. The guide image is an image of the starting plane with images of the starting point and the end of the surgical instrument. The user can observe the guide image so as to see how the end of the surgical instrument moves in the starting plane so that the user knows how to move the end of the surgical instrument to the starting point. Another possibility is that the alignment system shows the direction in which the end of the surgical instrument must be moved in order to reach the starting point, for example by indicating the desired direction by means of arrows. The user need not take into account displacement of the end of the surgical instrument parallel to the alignment line. Thus, it is much easier to move the end of the surgical instrument in a direction which is limited to one plane, i.e. the starting plane, than to move the end through the three-dimensional space. The starting plane always contains the end of the surgical instrument. The starting plane can be selected by selecting an auxiliary plane which is situated a predetermined, fixed distance from the end of the surgical instrument. The starting plane is then the plane extending parallel to the auxiliary plane at the predetermined, fixed distance from the auxiliary plane. For example, the auxiliary plane can be chosen so as to extend through a predetermined point on the surgical instrument which is situated at the predetermined, fixed distance from the end of the surgical instrument.

The starting plane moves in space in dependence on the movement of the surgical instrument. When the starting plane changes relative to the patient, the position of the starting point relative to the patient also changes, but for practically all surgical interventions it is not important where on the alignment line the starting point is situated. The alignment system reproduces the instantaneous position of the end of the surgical instrument and the position of the starting point. This enables the user to move the surgical instrument to the starting position quickly and accurately in a controlled manner.

The surgical instrument is, for example an instrument used to perform the relevant surgical intervention. The surgical instrument may also be a pointer which is positioned in the starting position and is subsequently replaced by the instrument whereby the surgical intervention is performed.

The image-guided surgery system according to the invention is suitable for use for a variety of surgical interventions, notably for neurosurgery such as cerebral operations and spinal operations.

The alignment system in a preferred embodiment of an image-guided surgery system according to the invention is arranged to reproduce the starting point substantially at the center of the guide image.

Because the starting point is reproduced substantially at the center of the guide image, the user can see very well how the surgical instrument must be moved so as to move the end to the starting point. Furthermore, the surgical instrument is hardly ever moved so that the reproduction of the end of the surgical instrument is moved (almost) out of the guide image, because the end of the surgical instrument is reproduced approximately at the center of the guide image during its displacement to the starting point. Moreover, there is not much risk of confusion between the starting point and the position of the end of the surgical instrument, because it is decided in advance that the starting point will be shown at the center of the guide image.

The alignment system in a preferred embodiment of an image-guided surgery system according to the invention is arranged to select the starting plane so as to extend substantially perpendicularly to the alignment line.

Consequently, the starting point will not be situated too far from the position of the end of the surgical instrument when the user starts to move the surgical instrument to the starting point, so that the surgical instrument need be displaced over a short distance only. Consequently, only a small amount of time is required to move the end of the surgical instrument accurately to the starting point. Moreover, it can be readily ensured that the starting point is not situated too far from the patient, so that the surgical instrument can be readily moved accurately to the target position along the alignment line.

The image display system in a preferred embodiment of an image-guided surgery system according to the invention is arranged to adjust the ratio of the distance between said end and the starting point to the distance between the reproduction of the end and the reproduction of the starting point in the guide image on the basis of the distance between said end and the starting point.

Via adjustment of the ratio, the guide image is reproduced with a magnification or reduction which is dependent on the distance between the end of the surgical instrument and the starting point. Preferably, a small magnification or even a reduction is used for as long as the end of the surgical instrument is still remote from the starting point, a (larger) magnification being used when the end of the surgical instrument reaches the vicinity of the starting point. The user can thus always see very well how the end of the surgical instrument must be displaced to the starting point because, for as long as the end of the surgical instrument is still remote from the starting point, the reproduction of the end will be situated within the guide image and the reproductions of the end of the surgical instrument and of the starting point can both be observed in the guide image. As soon as the end of the surgical instrument reaches the vicinity of the starting point, they will both be suitably separately reproduced in the guide image. Preferably, the reproduction of the guide image is step-wise enlarged as the end of the surgical instrument approaches the starting point.

The alignment system in a preferred embodiment of an image-guided surgery system according to the invention includes a rotatable alignment member for supporting the surgical instrument, the end of the surgical instrument being retained in a fixed position in the alignment member which is arranged to lock the end of the surgical element in the starting point, the alignment system being arranged to select the starting plane so as to extend through said fixed position in the alignment member.

The starting plane through the fixed position in the alignment member contains the end of the surgical instrument, because this end is retained in said fixed position relative to the alignment member. When the alignment member locks the end of the surgical instrument in the starting point, rotation of the surgical instrument about the end is still possible. The surgical instrument is oriented in the direction of the alignment line by rotating the alignment member supporting the surgical element.

The alignment system in a preferred embodiment of an image-guided surgery system according to the invention is arranged to reproduce a distance between the end of the surgical instrument and the target position.

The surgical instrument can thus be easily moved in the direction of the alignment line until the target position is reached. This is attractive notably when a biopsy is performed. The surgical instrument then consists of a biopsy needle which is positioned in the target position where it takes a sample of the tissue. The alignment system in a preferred embodiment of an image-guided surgery system according to the invention includes an instrument holder which is arranged to adjust the distance between the end of the surgical instrument and the target position while maintaining the orientation of the surgical instrument in the direction of the alignment line.

Such an instrument holder supports the surgical instrument. It enables accurate and easy displacement of the surgical instrument in the direction of the alignment line so as to reach the target position without excessive risk to the patient.

The invention also relates to a method of aligning a surgical instrument comprising the of: driving an alignment line through a target position, selecting a staring plane through an end of a surgical instrument, deriving a starting point of the alignment line and in the staring plane, and reproducing a position of said end and of said starting point relative to one another in the staring plane.

The method according to the invention achieves easier, faster and more accurate alignment of the surgical instrument, as compared to the alignment performed with the known image-guided surgery system.

BRIEF DESCRIPTION OF THE DRAWING

These and other aspects of the invention will be illustrated with reference to the following embodiments and the accompanying drawing; the Figure shows diagrammatically an image-guided surgery system in which the invention is used.

DETAILED DESCRIPTION OF THE PREFERRED EMBODIMENTS

The image-guided surgery system includes a position measuring system with a camera unit 10 and two CCD image sensors 11. The camera unit 10 is mounted on a patient table 30. The camera unit 10 forms images of the surgical instrument 20 from different directions. The surgical instrument is provided with a plurality of, for example three infrared emitting diodes (IREDs) 19. The CCD image sensors produce image signals, notably electronic video signals, which represent the individual images of the surgical instrument 20, notably of the IREDs 19. The position measuring system also includes a computer 12 for deriving the position of the surgical instrument from the image signals. Image information of the patient 21 to be examined or treated is stored in an image memory 13. The image information concerns, for example MRI and/or CT images formed before or during the surgical treatment. Marks 22 notably formed by fiducial markers, on or in the patient 21 are also reproduced in the images of the patient. The positions of the marks 22 are measured by means of the position measuring system, for example by pointing out the marks by means of the surgical instrument. The computer 12 derives the relation between positions in or on the patient 21 and the corresponding positions in the images from the positions of the marks and the positions of the images of the marks in the images formed. On the basis of the measured position of the surgical instrument 20 and said relation, the image processor 14 forms an image signal which represents an image which shows image information of the patient 21 and also the instantaneous position of the surgical instrument 20 in the patient. The computer 12, the image memory 13 and the image processor are included in a data processor 9 whereto a monitor 8 is connected. The image signal is applied to the monitor 8. Image information of the patient 21, showing where the surgical instrument 20 is situated, is displayed on the monitor 8. The user can thus move the surgical instrument 20 within the patient 21 without having a direct view of the instrument and without risk of unnecessary damaging of tissue.

The image-guided surgery system according to the invention includes an alignment system by means of which the user can readily position the surgical instrument 20 in a suitable starting position B. The alignment system includes the camera unit 10, the computer 12, the image processor 14 and the monitor 8. Preferably, the alignment system also includes a system of arms 6 which supports the alignment member 7. Prior to the surgical intervention, for example a biopsy, the user selects the target position T and also the alignment line 1 from the pre-recorded image information. The alignment line 1 passes through the target position T and through the entrance position E. The entrance position E is selected to be such that the target position T can be readily reached along the alignment line, without unnecessary damaging of tissues or without excessive risk to the patient. The position measuring system 10, 12 measures the position of the end U of the surgical instrument. The computer 12 calculates the position of the target position T and the entrance position E from the positions of the reproductions of the target and entrance position selected in the image information by the user. The computer 12 subsequently calculates the starting plane α which extends through the instantaneous position U of the end 25 of the surgical instrument and preferably perpendicularly to the alignment line 1. The computer 12 also calculates the point of intersection between the alignment line 1 and the starting plane α; this point of intersection is the starting point B. The computer 12 then calculates the positions of the end U and the starting point B in the starting plane α. On the basis of these positions, the image processor forms an image signal which represents the guide image. Such a guide image is displayed on the monitor 18 and shows the position U of the end 25 and the position of the starting point B in the starting plane α. In the example shown in the Figure, the position of the starting point is shown at the center of the image, denoted by a circle, and the position of the end 25 is denoted by a cross. The user can readily move the end 25 of the surgical instrument 20 to the starting position B while observing the guide image. Adjacent to or instead of the position of the starting position B and the position U of the end 25, the image processor 14 can provide arrows 26 in the guide image on the monitor 8 so as to indicate the directions in which the end 25 must be moved in the starting plane α so as to reach the starting point B. It is not essential that the end 25 of the surgical instrument is moved parallel to the direction of the alignment line during its displacement to the starting position B by the user. The computer automatically adapts the position of the starting plane α by ensuring that the starting plane α always extends through the position U of the end 25. The starting point is automatically adapted to the movement of the starting plane α because the starting point is the point of intersection between the alignment line 1 and the starting plane α. It has been found that it is not very important where exactly on the alignment line 1 the starting point B is situated.

The computer 12 also calculates the distance between the end 25 of the surgical instrument and the target position T; this calculation preferably takes place when the end 25 has been placed in the starting position B. On the basis of this distance the image processor 14 controls the monitor 8 so as to provide a depth indication. The depth indication is, for example a scale graduation 27 on which the distance between the end 25 and the target position T is indicated by means of a pointer 28. The user can thus see on the monitor how far the end 25 must be moved in the direction of the alignment line so as to reach the target position T.

The alignment system also includes a system of arms 6 with a plurality of arms 31 which are rotatably coupled to one another, for example by means of hinges 32. The alignment member 7 is secured to an end 29 of the system of arms. The hinges can be locked so as to retain the alignment member 7 in a desired position. The surgical instrument 20 fits in an opening 33 in the alignment member 7. The alignment member 7 is, for example a sphere in which a cylindrical channel 33 is recessed so as to extend through the center of the sphere. Using the alignment member 7, the surgical instrument 20 can be readily aligned in the direction of the alignment line 1, the end being retained in the starting position B. By sliding the surgical instrument 20 through the channel 33, the end 25 is moved accurately in the direction of the alignment line 1 to the target position T. When such an alignment member is used, the depth indication can be simply used to arrange the alignment member at a fixed distance from the target position T. Such a fixed distance is, for example a standard length of the biopsy needle. When the alignment member has been arranged at the desired, fixed distance from the target position on the basis of the depth indication, the biopsy needle moved into the patient via the alignment member will accurately reach the target position.

All references cited herein are incorporated herein by reference in their entirety and for all purposes.

We claim:

1. An image-guided surgical alignment system for producing a display of the alignment of a surgical instrument with respect to a patient, comprising:

position measuring means for providing position signals representing positions and/or orientations of the surgical instrument;

an image memory for providing patient images;

a computer responsive to the provided position signals and patient images to supply image signals; and a video display unit for displaying images in response to the image signals;

wherein the computer is operative to
- (i) derive a spatial alignment line for the surgical instrument from a target position and an entrance position, the target and entrance positions being specified on a patient image provided by the image memory,
- (ii) select a spatial starting plane passing through a determined position of an end of the surgical instrument, and
- (iii) derive a starting point on the alignment line and in the starting plane;

the image signals supplied by the computer being based on a current position of said end of the surgical instrument and information for guiding positioning thereof to the starting point by movement in the starting plane.

2. An image-guided surgical alignment system as claimed in claim 1, in which the image signals supplied by the computer cause movement of the starting plane together with a displacement of the end of the surgical instrument.

3. An image-guided surgical alignment system as claimed in claim 2, in which the image signals supplied by the computer reproduce a guide image of said end of the surgical instrument and the starting point in the starting plane on the video display unit.

4. An image-guided surgical alignment system as claimed in claim 3 in which the image signals supplied by the computer reproduce the starting point substantially at the center of the guide image.

5. An image-guided surgical alignment system as claimed in claim 4 in which the ratio of (i) the distance between said end and the starting point to (ii) the distance between the reproduction of the end and the reproduction of the starting point in the guide image is adjusted to produce a degree of magnification or reduction dependent on the distance between said end and the starting point.

6. An image-guided surgical alignment system as claimed in claim 1, in which the image signals supplied by the computer reproduce a guide image of said end of the surgical instrument and the starting point in the starting plane on the video display unit.

7. An image-guided surgical alignment system as claimed in claim 6 in which the image signals supplied by the computer reproduce the starting point substantially at the center of the guide image.

8. An image-guided surgical alignment system as claimed in claim 7 in which the ratio of (i) the distance between said end and the starting point to (ii) the distance between the reproduction of the end and the reproduction of the starting point in the guide image is adjusted to produce a degree of magnification or reduction dependent on the distance between said end and the starting point.

9. An image-guided surgical alignment system as claimed in claim 6 in which the ratio of (i) the distance between said end and the starting point to (ii) the distance between the reproduction of the end and the reproduction of the starting point in the guide image is adjusted to produce a degree of magnification or reduction dependent on the distance between said end and the starting point.

10. An image-guided surgical alignment system as claimed in claim 1, in which the starting plane is selected so as to extend perpendicular to the alignment line.

11. An image-guided surgical alignment system as claimed in claim 1, further comprising a rotatable alignment member for supporting the surgical instrument, the alignment member being arranged to retain the end of the surgical instrument in a fixed position therein, the alignment member further being arranged to lock the end of the surgical instrument to the starting point; the computer selecting the starting plane so as to extend through said fixed position in the alignment member.

12. An image-guided surgical alignment system as claimed in claim 1, in which the image signals supplied by the computer produce on said display unit a display of the distance between the end of the surgical instrument and the target position.

13. An image-guided surgical alignment system as claimed in claim 1, further comprising an instrument holder for adjusting the distance between the end of the surgical instrument and the target position while maintaining the orientation of the surgical instrument in the direction of the alignment line.

14. A method of producing a display of the alignment of a surgical instrument with respect to a patient, comprising:

- determining a current spatial position of the surgical instrument;
- storing patient images in an image memory;
- deriving a spatial alignment line for the surgical instrument from a target position and an entrance position, the target and entrance positions being specified on one or more patient images provided by the image memory;
- selecting a spatial starting plane passing through a determined position of an end of the surgical instrument;
- deriving a starting point on the alignment line and in the starting plane; and
- producing on a video display unit a display of the current spatial position of said end of the surgical instrument together with information for guiding positioning thereof to the starting point by movement in the starting plane.

* * * * *